US00PP23171P3

(12) United States Plant Patent

Rogmans et al.

(10) Patent No.: US PP23,171 P3

(45) Date of Patent: Nov. 6, 2012

(54) *EICHHORNIA CRASSIPES* PLANT NAMED 'JOHANN SCHOOFS SEN'

(50) Latin Name: *Eichhornia crassipes*
Varietal Denomination: Johann Schoofs Sen.

(75) Inventors: Maria Rogmans, Kalkar (DE); Hermann-Josef Wilhelm, Kalkar (DE)

(73) Assignee: Maria Rogmans, Kalkar (DE)

( * ) Notice: Subject to any disclaimer, the term of this patent is extended or adjusted under 35 U.S.C. 154(b) by 0 days.

(21) Appl. No.: 12/801,390

(22) Filed: Jun. 7, 2010

(65) Prior Publication Data

US 2011/0010812 P1 Jan. 13, 2011

(30) Foreign Application Priority Data

Jun. 5, 2009 (QZ) ..... PBR 20090985

(51) Int. Cl.
*A01H 5/00* (2006.01)

(52) U.S. Cl. ..... Plt./342

(58) Field of Classification Search ..... Plt./342, Plt./263.1, 395
See application file for complete search history.

*Primary Examiner* — Kent L Bell

(74) *Attorney, Agent, or Firm* — Buchanan Ingersoll & Rooney PC

(57) ABSTRACT

A new *Eichhornia crassipes* plant named 'Johann schoofs Sen' is provided which is well suited to serve as a biomass renewable energy source. The plant is particularly well suited to metabolize carbon dioxide from emissions. A free-floating small compact mat-like growth habit is displayed with an intertwined root ball. A typical leaf petiole is absent, and the roots are finely structured. The leaves are dark green in coloration, and the plant survives well under low-light conditions. The plant generates itself from new shoots and commonly can double its biomass in approximately 10 to 14 days.

2 Drawing Sheets

Botanical/commercial classification: *Eichhornia crassipes*/Water Hyacinth cv. Johann Schoofs Sen.

BACKGROUND OF THE INVENTION

Common Water Hyacinth (i.e., *Eichhornia crassipes*) is recognized to be a free-floating perennial aquatic plant that is native to tropical and sub-tropical South America. The plant has been naturalized in most of the southern United States. Feathery, long freely hanging roots commonly are displayed. The plant reproduces primarily by way of runners or stolons which form daughter plants. In recent years, interest has focused on the use of plants for possible renewable energy source, as well as for industrial utilization. *Eichhornia crassipes* plants have been included in this interest.

Such *Eichhornia crassipes* plants are generally adapted to produce carbohydrates through the mixotropic conversion of carbon dioxide while deriving nourishment via both autotropic and heterotropic mechanisms. For instance, organic matter (even contamination and waste) present in water and carbon dioxide from the air can be combined by the plants. Carbohydrates in the water are broken down into simple sugars. During growth phosphorus and nitrogen are consumed. Unwanted substances are removed from the water. Upon harvest, the resulting plants can be burned directly to yield a source of fuel or energy. Alternatively, the plants can be processed to form a biofuel wherein the plants serve as a feedstock for ethanol or methane production.

Less reliance upon fossil fuels is required upon the utilization of such energy source. The plant further serves as a natural water purifier.

It is recognized that common *Eichhornia crassipes* plants commonly possess a petiole of several centimeters in length between the bulb and leaf. Additionally, a non-compact plant growth habit commonly is displayed.

SUMMARY OF THE INVENTION

A combination of naturally-occurring crossing and extensive selection was utilized to form the new *Eichhornia crassipes* plant of the present invention in the absence of genetic engineering and intentional chemically-induced mutagenesis. Naturally-occurring *Eichhornia crassipes* (Mart.) Solms plants were admixed in a common water compartment. Such plants were cultivated at a high population density to yield a higher population under conditions designed to encourage blossoming and naturally-occurring fertilization among adjoining plants. Naturally-occurring spontaneous mutations may have also occurred under such conditions. Thereafter the plants were subjected to reduced light and reduced nutrients. The number of surviving plants was drastically reduced and reproduction was limited to that of naturally-occurring asexual means. Thereafter only a few *Eichhornia crassipes* plants were living and each was found to be physically and biologically different from each other. From among the surviving plants a single distinctive plant of the new variety of the present invention was selected, was carefully preserved, and was grown under conditions which precluded reproduction by sexual means.

The new plant of the present invention was found to display the following combination of characteristics:

(a) is free-floating and displays a smaller and more compact and darker green growth habit, (b) unlike typical *Eichhornia crassipes* plants lacks a typical leaf petiole, (c) displays finely structured roots, (d) is capable of rapid asexual propagation through the prolific growth of stolons which become unattached from mother plants, and (e) is well suited to serve as a highly productive biomass renewable energy source.

The plant is particularly well-suited to metabolize carbon dioxide from emissions with a simultaneous increase in mass. Also, nourishment can be derived from substances present in the water, including water contaminants.

The propensity for the new plant to grow and to increase in mass is particularly noteworthy. The small compact growth habit enables the presence of a large number of individual plants in a given production area. As the plants spontaneously asexually reproduce at a high growth rate, the resulting mass is rapidly enlarged. The plant commonly is capable of doubling its mass in approximately 10 to 14 days. The finely structured root structure enables the efficient absorption of nutrients. Such efficiency is evidenced by a strong green coloration that facilitates the conduct of photosynthesis even under reduced light conditions. Initially, carbon dioxide is removed from the atmosphere and is bound and thereafter chemical components are extracted from the water. The plants contain high protein and high carbohydrate concentrations which are produced at a rapid growth rate. As carbon dioxide is captured from the atmosphere, global warming concerns are diminished, and water quality is improved. Periodic regular harvesting ensures a continuous new supply of new young plants.

The new plant of the present invention has been asexually reproduced at Kalkar, Germany, and at Naktiunbouw, The Netherlands. Such asexual reproduction takes place spontaneously as stolons are formed, grow, and thereafter become unattached to create identical new plants. It has been found that the new plant undergoes such asexual reproduction in a true-to-type manner.

The new plant has been named 'Johann Schoofs Sen.'

DESCRIPTION OF THE PHOTOGRAPHS

The accompanying photographs illustrate typical plants of the new variety of the present invention, as well as a typical common *Eichhornia crassipes* plant for comparative purposes.

DETAILED DESCRIPTION

The chart used in the identification of colors is that of The Royal Horticultural Society (R.H.S. Colour Chart), London, England (1995 Edition or equivalent). The observed plants were grown at Kalkar, Germany, and at Naktiunbouw, The Netherlands.

Botanical classification: *Eichhornia crassipes*, cv Johan Schoofs Sen.

Growth habit: Floats on the surface of water with the roots being substantially completely submerged. The overall growth habit is substantially smaller and substantially more compact than that of typical *Eichhornia crassipes* plants.

Figure 2:
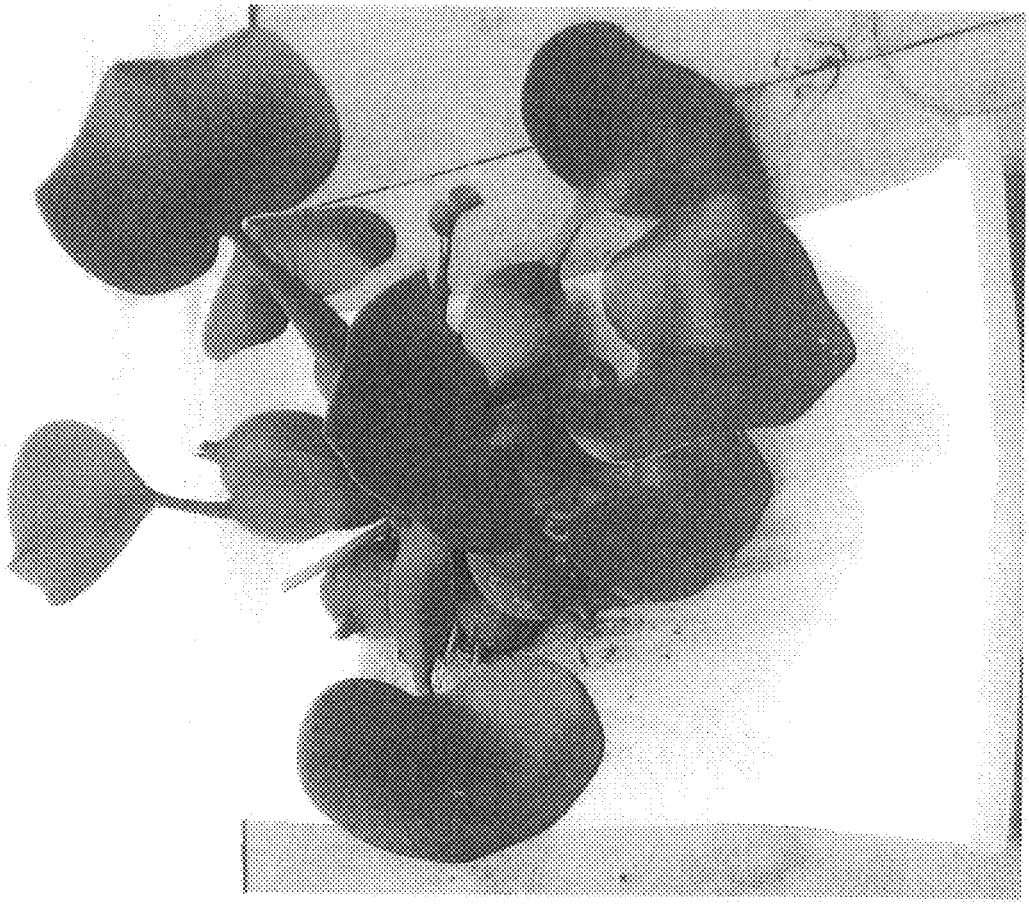
FIG. 2 illustrates for comparative purposes a typical common *Eichhornia crassipes* plant wherein a relatively non-compact growth habit is apparent together with typical extended leaf petioles.
Figure 1:
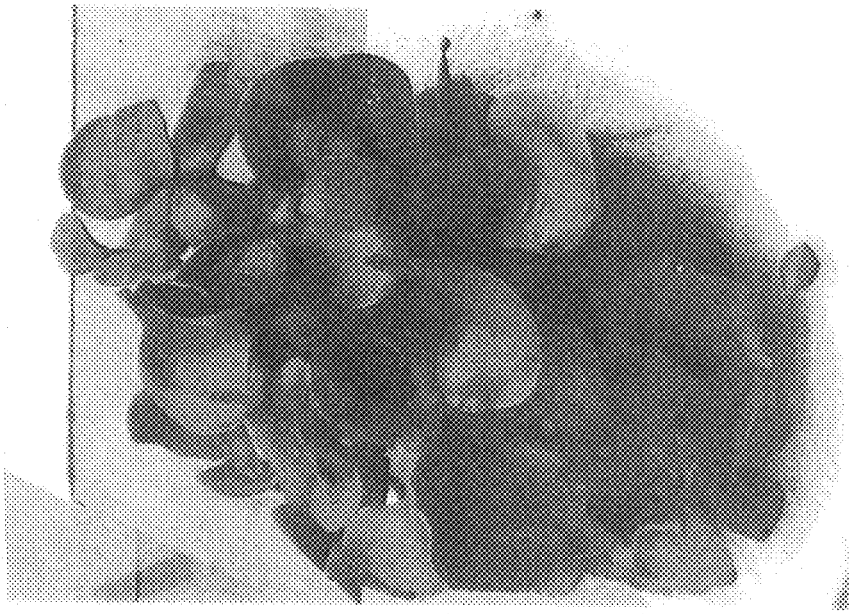
FIG. 1 illustrates a typical plant of the new variety wherein the more compact and darker green growth habit is apparent in the substantial absence of common leaf petioles.
Figure 3:
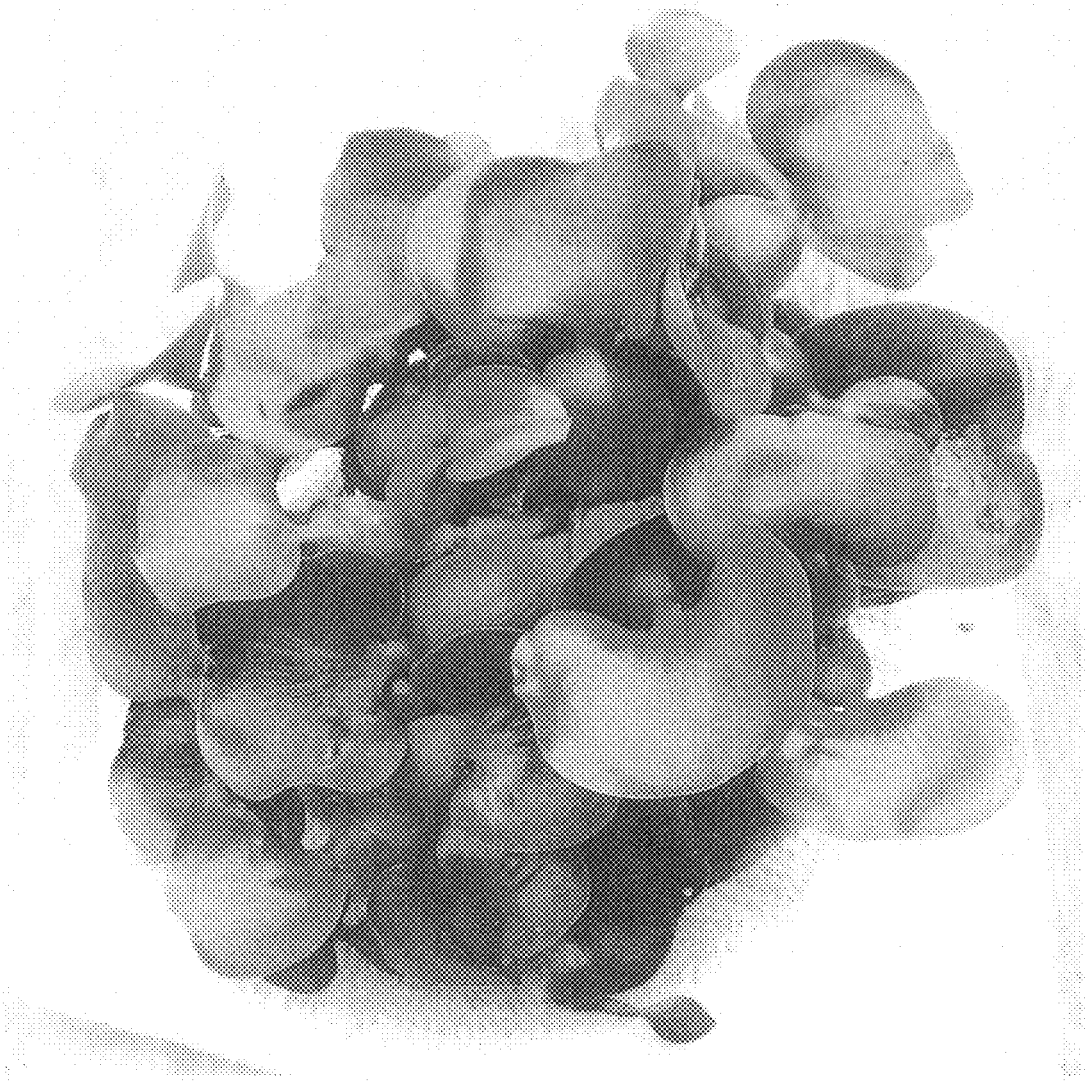
FIG. 3 illustrates a closer view of a representative plant of the new variety wherein the compact nature of the vegetative mass is further apparent.

Plant characteristics: The dark green leaves are generally elliptic in configuration, are slightly concave and are slightly wavy in appearance. The leaves are displayed in abundance and are smaller than those typically displayed by *Eichhornia crassipes*. The leaves commonly are approximately 3 to 9 cm in length and approximately 2.5 to 4.5 cm in width. The coloration of the upper leaf surface commonly ranges from near Green Group 137A to 137B to 137C. The coloration of the under leaf surface is lighter green and commonly is near Yellow-Green Group 144A. Such leaf coloration on the upper surface is darker than that commonly displayed by *Eichhornia crassipes*. The leaf tips sometimes are slightly indented and bases of the leaves commonly are obtuse to cordate in configuration. The texture of the leaves is leathery, succulent, and firm. The upper surfaces of the leaves display a silky matte appearance. Somewhat random venation is frequently apparent on the upper surface of the leaves. Unlike typical plants of *Eichhornia crassipes* the leaves are positioned almost directly on the bulbs. Accordingly, as illustrated, a typical leaf petiole distinctively is either absent or ultra short. See the comparison between the plants of FIG. 2 and FIG. 3. The petioles commonly are near Yellow-Green Group 145A in coloration. The thick bulbs are onion-like and flattened-oval in appearance unlike the long and slender bulbs typically displayed by *Eichhornia crassipes*. The bulbs efficiently retain food reserves which enable the plant to grow and to well survive. Such bulbs of the new variety commonly number approximately 25 to 30 or more on a mature plant and commonly are approximately 1.5 to 1.8 cm in height and approximately 4 to 4.5 cm in width at the widest point. On the top surface the coloration of the bulbs commonly is near Green Group 137C, and on the under surface near Yellow-Green Group 145A. The roots of the new variety form a coherent root ball and generally are more finely structured than those typical of *Eichhornia crassipes* thereby providing a greater active surface area which facilitates the efficient uptake of chemical components dissolved in the water where the plant is situated. When growing the root ball is substantially completely covered by water. This root structure and disposition readily facilitate efficient photosynthesis even when plants of the new variety are grown under low light conditions. Flowering typically does not occur under the growing conditions utilized and inflorescence is not available for characterization. However, when flowering occurs based upon available information, the resulting flowers are believed to be typical of the species.

Asexual reproduction: The new variety is well suited for growing in a closed bioreactor with a daily harvesting of approximately 7 to 10 percent of the plant contents. Under such growing conditions flowering is effectively suppressed. The plants when present in a closed bioreactor spontaneously undergo asexual propagation as stolons are formed, grow, and thereafter become unattached from mother plants to create identical new plants.

The invention claimed is:

1. A new and distinct *Eichhornia crassipes* plant, substantially as illustrated and described.

* * * * *